(12) United States Patent  
Mazda et al.

(10) Patent No.: US 8,323,319 B2
(45) Date of Patent: Dec. 4, 2012

(54) VERTEBRAL FIXING SYSTEM

(75) Inventors: Keyvan Mazda, Paris (FR); Régis Le Couedic, Andresy (FR)

(73) Assignee: Zimmer Spine S.A.S., Bordeaux (FR)

( * ) Notice: Subject to any disclaimer, the term of this patent is extended or adjusted under 35 U.S.C. 154(b) by 149 days.

(21) Appl. No.: 12/854,753

(22) Filed: Aug. 11, 2010

(65) Prior Publication Data

US 2011/0034956 A1 Feb. 10, 2011

Related U.S. Application Data

(60) Division of application No. 12/358,748, filed on Jan. 23, 2009, now Pat. No. 7,959,654, which is a continuation of application No. 10/521,914, filed as application No. PCT/FR03/02307 on Jul. 22, 2003, now Pat. No. 7,481,828.

(30) Foreign Application Priority Data

Jul. 23, 2002 (FR) ...................................... 02 09317

(51) Int. Cl.
*A61B 17/88* (2006.01)
*A61B 17/70* (2006.01)
(52) U.S. Cl. ....................................... 606/279; 606/263
(58) Field of Classification Search .......... 606/246–279, 606/300–319
See application file for complete search history.

(56) References Cited

U.S. PATENT DOCUMENTS

| 902,040 A | 10/1908 | Wychoff |
|---|---|---|
| 1,346,940 A | 7/1920 | Collins |
| 2,049,361 A | 7/1936 | Johan |
| 4,570,618 A | 2/1986 | Wu |
| 5,030,220 A | 7/1991 | Howland |
| 5,304,178 A | 4/1994 | Stahurski |
| 5,356,412 A | 10/1994 | Golds et al. |
| 5,413,576 A | 5/1995 | Rivard |
| 5,449,361 A | 9/1995 | Preissman |
| 5,669,917 A | 9/1997 | Sauer et al. |

(Continued)

FOREIGN PATENT DOCUMENTS

DE 19716504 12/1998

(Continued)

OTHER PUBLICATIONS

Office Action issued in U.S. Appl. No. 11/877,160, mailed Nov. 26, 2010, 10 pages.

(Continued)

*Primary Examiner* — Eduardo C Robert
*Assistant Examiner* — Stuart S Bray
(74) *Attorney, Agent, or Firm* — Seager Tufte & Wickhem LLC

(57) ABSTRACT

Embodiments disclosed herein provide a method of placing a vertebral fixing system on a vertebra. The vertebral fixing system comprises a connecting part with members forming a space into which a rod may be inserted. The members are moveable relative to each other. A portion of a ligature may be passed through the connecting part to form a loop extending from the connecting part. When the rod is inserted in the space between the members, the ligature may be tensioned against the rod. The members of the connecting part may be driven together to hold the ligature in place. An adjustable locking means may be utilized to fix simultaneously in position the connecting part relative to the rod and at least one portion of the ligature relative to the connecting part, so as to prevent relative displacement of the rod and the vertebra in opposite directions.

24 Claims, 3 Drawing Sheets

U.S. PATENT DOCUMENTS

Figure 1:
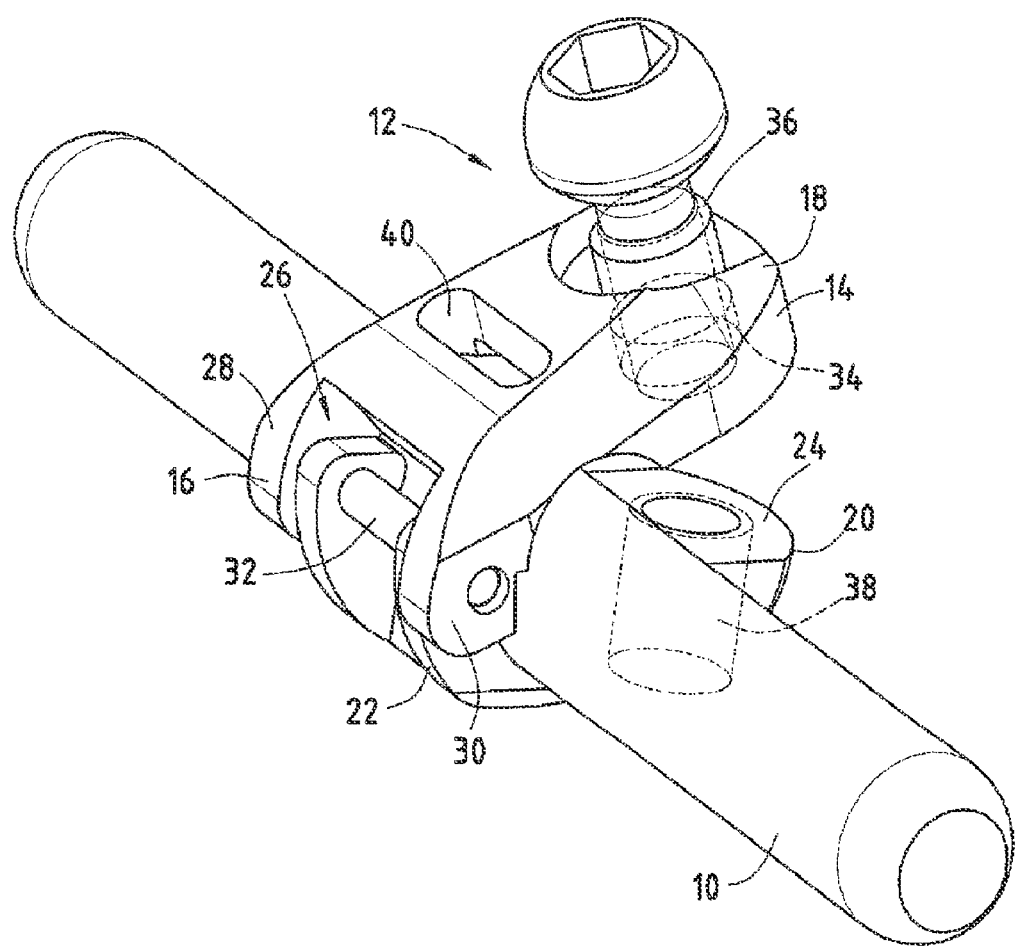

| | | | |
|---|---|---|---|
| 5,702,399 | A | 12/1997 | Kilpeta et al. |
| 5,720,751 | A | 2/1998 | Jackson |
| 5,772,663 | A | 6/1998 | Whiteside et al. |
| RE36,221 | E | 6/1999 | Breard |
| 5,935,133 | A | 8/1999 | Wagner et al. |
| 5,938,663 | A | 8/1999 | Petreto |
| 5,964,769 | A | 10/1999 | Wagner et al. |
| 6,053,921 | A | 4/2000 | Wagner et al. |
| 6,086,590 | A | 7/2000 | Margulies et al. |
| 6,099,527 | A | 8/2000 | Hochschuler et al. |
| 6,146,386 | A | 11/2000 | Blackman et al. |
| 6,179,838 | B1 | 1/2001 | Fiz |
| 6,228,096 | B1 | 5/2001 | Marchand |
| 6,241,740 | B1 | 6/2001 | Davis et al. |
| 6,277,120 | B1 | 8/2001 | Lawson |
| 6,299,613 | B1 | 10/2001 | Ogilvie et al. |
| 6,309,390 | B1 | 10/2001 | Le Couedic et al. |
| 6,391,030 | B1 | 5/2002 | Wagner et al. |
| 6,447,518 | B1 | 9/2002 | Krause et al. |
| 6,478,798 | B1 | 11/2002 | Howland |
| 6,514,255 | B1 | 2/2003 | Ferree |
| 6,547,770 | B2 | 4/2003 | Carlsson et al. |
| 6,547,790 | B2 | 4/2003 | Harkey, III et al. |
| 6,569,164 | B1 | 5/2003 | Assaker et al. |
| 6,569,171 | B2 | 5/2003 | DeGuillebon et al. |
| 6,605,091 | B1 | 8/2003 | Iwanski |
| 6,616,669 | B2 | 9/2003 | Ogilvie et al. |
| 6,656,179 | B1 | 12/2003 | Schaefer et al. |
| 6,656,185 | B2 | 12/2003 | Gleason et al. |
| 6,682,533 | B1 | 1/2004 | Dinsdale et al. |
| 6,689,140 | B2 | 2/2004 | Cohen |
| 6,695,852 | B2 | 2/2004 | Gleason |
| 6,746,452 | B2 | 6/2004 | Tuke et al. |
| 6,773,438 | B1 | 8/2004 | Knodel et al. |
| 6,946,000 | B2 | 9/2005 | Senegas et al. |
| 7,481,828 | B2 | 1/2009 | Mazda et al. |
| 7,699,874 | B2 | 4/2010 | Young |
| 7,959,654 | B2 | 6/2011 | Mazda |
| 2002/0116013 | A1 | 8/2002 | Gleason et al. |
| 2002/0198538 | A1 | 12/2002 | Kortenbach et al. |
| 2003/0195628 | A1 | 10/2003 | Bao et al. |
| 2004/0087979 | A1 | 5/2004 | Field et al. |
| 2004/0138666 | A1 | 7/2004 | Molz, IV et al. |
| 2005/0070958 | A1 | 3/2005 | Swayze et al. |
| 2005/0085815 | A1 | 4/2005 | Harms |
| 2005/0131404 | A1 | 6/2005 | Mazda |
| 2005/0154403 | A1 | 7/2005 | Sauer et al. |
| 2005/0177156 | A1 | 8/2005 | Timm et al. |
| 2005/0228375 | A1 | 10/2005 | Mazda et al. |
| 2006/0235391 | A1 | 10/2006 | Sutterlin, III |
| 2007/0016190 | A1 | 1/2007 | Martinez et al. |
| 2007/0088359 | A1 | 4/2007 | Woods et al. |
| 2007/0299445 | A1 | 12/2007 | Shadduck et al. |
| 2008/0058812 | A1 | 3/2008 | Zehnder |
| 2008/0125780 | A1 | 5/2008 | Ferree |
| 2008/0140133 | A1 | 6/2008 | Allard et al. |
| 2008/0208256 | A1 | 8/2008 | Thramann |
| 2009/0131985 | A1 | 5/2009 | Mazda |
| 2009/0138048 | A1 | 5/2009 | Baccelli et al. |

FOREIGN PATENT DOCUMENTS

| | | |
|---|---|---|
| EP | 0780096 | 6/1997 |
| EP | 1815812 | 8/2007 |
| FR | 522040 | 7/1921 |
| FR | 26156 | 9/1932 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| GB | 2269753 | 2/2004 |
| JP | 2001299770 | 10/2001 |
| WO | WO9416635 A1 | 8/1994 |
| WO | 0154599 | 8/2001 |
| WO | WO0207622 | 1/2002 |
| WO | 0209604 A1 | 2/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO03103519 A1 | 12/2003 |
| WO | WO2004010881 A1 | 2/2004 |
| WO | WO2005120277 A1 | 12/2005 |
| WO | WO2007034112 A1 | 3/2007 |
| WO | WO2007036657 | 4/2007 |
| WO | WO2007099258 A2 | 9/2007 |

OTHER PUBLICATIONS

Office Action issued in U.S. Appl. No. 11/996,918, mailed Feb. 14, 2011, 12 pages.

Office Action issued in U.S. Appl. No. 12/059,634, mailed Feb. 15, 2011, 14 pages.

Office Action issued in U.S. Appl. No. 12/408,592, mailed Feb. 18, 2011, 17 pages.

Notice of Allowance issued in U.S. Appl. No. 12/358,748, mailed Feb. 23, 2011, 5 pages.

Office Action issued in U.S. Appl. No. 12/408,592, mailed Sep. 22, 2011, 24 pages.

Office Action issued in U.S. Appl. No. 12/059,634, mailed Oct. 5, 2011, 12 pages.

Office Action issued in U.S. Appl. No. 12/059,634, mailed Jun. 22, 2011, 15 pages.

European Search Report issued in European Patent Application No. EP08305124.3, Oct. 24, 2008, 4 pages.

Office Action issued in U.S. Appl. No. 11/996,918, mailed Aug. 17, 2011, 11 pages.

Notice of Allowance issued in U.S. Appl. No. 12/375,265, mailed Aug. 25, 2011, 10 pages.

English Translation of International Preliminary Report for PCT/FR2006/050898 on Patentability Chapter I, dated Apr. 29, 2008, 6 pages.

English Translation of International Preliminary Report on Patentability Chapter I for PCT/FR2006/050909, dated Apr. 8, 2008, 5 pages.

English Translation of the Written Opinion of the International Search Authority for PCT/FR2006/050909, dated Apr. 2, 2008, 4 pages.

English Translation of the Written Opinion of the International Search Authority for PCT/FR2006/050898, dated Apr. 28, 2008, 5 pages.

European Search Report for EP 08305326, dated Nov. 12, 2008, 3 pages.

European Search Report for EP 2052689, dated Apr. 15, 2008, 6 pages.

European Search Report issued in EP 08305326 on Nov. 18, 2006, 5 pages.

French Preliminary Search Report and Written Opinion for FR200650609, dated Jun. 30, 2006, 5 pages.

International Search Report for WO2009053423, dated May 19, 2009, 4 pages.

International Search Report mailed Nov. 24, 2008 for PCT/EP2008/063682, 3 pages.

International Search Report for PCT/FR2006/050909 published as WO/2007/034112, dated Jan. 24, 2007, 3 pages.

Office Action for U.S. Appl. No. 10/521,914, dated Dec. 29, 2006, 21 pages.

Office Action for U.S. Appl. No. 10/521,914, dated Mar. 19, 2008, 7 pages.

Office Action for U.S. Appl. 10/521,914, dated Jun. 16, 2006, 13 pages.

Office Action for U.S. Appl. No. 10/521,914, dated Jul. 30, 2007, 13 pages.

International Search Report and Written Opinion for PCT/US2009/038977, mailed Jul. 22, 2009, 13 pages.

Korean Examination report for Korean Patent Application No. 1020057001238, mailed Feb. 23, 2010, 3 pages.

French Preliminary Search Report for FR0209317, dated Apr. 9, 2003, 1 page.

French Preliminary Search Report for FR0509629 mailed Jun. 9, 2006, 2 pages.

International Search Report for FR200302307, dated Jan. 2, 2004, 2 pages.
Australian Search Report for Australian Patent Application No. 2003267529, dated Nov. 15, 2007, 2 pages.
French Preliminary Search Report FR0509570, dated Jun. 29, 2006, 2 pages.
International Search Report for PCT/FR2006/050898, dated Feb. 2, 2007, 2 pages.
Written Opinion for PCT/US2009/038977, mailed Feb. 24, 2010, 7 pages.
European Search Report for European Patent Application No. 07 301 454.0, mailed Sep. 25, 2008, 8 pages.
Partial European Search Report issued in European Application No. 07 301 483.9, completed Apr. 15, 1998, mailed Apr. 23, 2008, 6 pages.
European Search Report and Search Opinion issued in European Application No. 07 301 483.9, completed Apr. 15, 1998, mailed Jul. 10, 2008, 10 pages.
International Search Report and Written Opinion issued in PCT Application No. PCT/EP2008/064344, completed Jan. 16, 2009, mailed May 19, 2009, 13 pages.
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 12 pages.
International Search Report and Written Opinion issued in International Patent Application No. PCT/EP2008/064344, published as WO/2008/053423, mailed May 19, 2009, 11 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Notice of Allowance issued in U.S. Appl. No. 11/877,160, mailed Oct. 31, 2011, 7 pages.
Notice of Allowance issued in U.S. Appl. No. 11/996,918, mailed Dec. 19, 2011, 9 pages.
Office Action issued in U.S. Appl. No. 11/877,160, mailed Apr. 12, 2011, 12 pages.

VERTEBRAL FIXING SYSTEM

CROSS-REFERENCE TO RELATED APPLICATIONS

This application is a divisional of U.S. patent application Ser. No. 12/358,748, filed Jan. 23, 2009, now U.S. Pat. No. 7,959,654, entitled "VERTEBRAL FIXING SYSTEM," which is a continuation of U.S. patent application Ser. No. 10/521,914, filed Jan. 20, 2005, now U.S. Pat. No. 7,481,828, entitled "VERTEBRAL FIXING SYSTEM," which is a National Stage Entry under 35 U.S.C. 371 of International Application No. PCT/FR2003/02307, filed Jul. 22, 2003, entitled "VERTEBRAL FIXING SYSTEM," which claims priority to French Application No. 02/09317, filed Jul. 23, 2002, entitled "SYSTEME DE FIXATION VERTEBRALE," all of which are fully incorporated herein by reference.

The present invention relates to a vertebral fixing system adapted to be mounted on a vertebra, and to a spine-straightening assembly using the system.

One field of application that is envisaged, is particularly but not exclusively, the treatment of scoliosis or, more generally, the correction of abnormal curvatures of the spine.

The spine is formed of superposed vertebrae, normally aligned along a vertebral axis, from the lumbar vertebrae to the cervical vertebrae, and each having a posterior wall from which projects a spinous process and two lateral edges from the walls of which there project ribs and/or transverse processes. If the spine of a person has abnormal curvature, the vertebrae are inclined relative to each other and relative to said vertebral axis. The lateral edges of the vertebrae on one side are therefore closer together and form a concave shape while the lateral edges on the other side are farther apart and form a convex shape.

To straighten the vertebral column, the lateral edges of the vertebrae on the concave side are moved away from one another and supported at distances from one another substantially equivalent to the distances between the lateral edges on the other side. Devices known in the art are used thereafter to hold the vertebrae relative to one another, and comprise screws that are inserted into the vertebrae or hooks that are inserted along the internal wall of the spinal canal and rods adapted to connects the screws or hooks.

Pairs of hooks are generally inserted into each vertebra, one on each side, near the pedicle; they have heads that project from the posterior wall of the vertebra, one on each side of the spinous process. The heads are tulip-shaped, for example, and are adapted to receive a rod that is immobilized by a nut that is screwed onto the head and bears on the rod. The heads of the hooks situated on either side of the spinous process are connected together and fixed in position by two rods parallel to each other and to the axis of the spine.

However, using such hooks is difficult because the operative must not under any circumstances touch the spinal cord that extends along the centre of the spinal canal, since that would result in paralysis of the patient.

Using screws reduces the risks of the procedure. The screws also have tulip-shaped heads and are inserted in pairs into the pedicles on each side of the spinous process on the posterior wall of the vertebrae. The screws therefore constitute fixing points on the vertebrae for holding them relative to one another. However, they must be inserted into the pedicles of the vertebrae, which in some cases are small or have deteriorated.

A problem that arises, and that the present invention aims to solve, is that of providing fixing points when it is not possible to insert screws into the vertebrae in the abnormal curvature region and when using hooks is too dangerous.

To achieve the above object, a first aspect of the present invention proposes a vertebral fixing system that comprises: a connecting part adapted to face said rib and/or said transverse process and to be connected to said rod, an elongate flexible ligature adapted to connect together said connecting part and at least one rib and/or one transverse process, and adjustable locking means fastened to said connecting part and adapted to fix simultaneously in position said connecting part relative to said rod and at least one portion of said ligature relative to said connecting part, so as to prevent relative displacement of said rod and said vertebra in opposite directions.

Thus one feature of the invention resides in the method of connecting said rod with said vertebrae using the connecting part that connects together the flexible ligature and said rod. The ligature, one end of which is connected to said rib and/or transverse process, is adapted to be immobilized in said connecting part by the adjustable locking means, which also fix said connecting part in position relative to said rod, with the result that relative displacement of said rod and said vertebra is prevented, at least in the opposite direction.

In a first embodiment of the invention, said connecting part includes a passage facing said rod and said ligature passes through the adjustable locking means to reduce the section of said passage in order to press said ligature against said rod and simultaneously to fix said connecting part and at least one portion of said ligature in position relative to said rod.

As a result of this feature of the invention, said ligature is adapted to be wedged between the wall of the passage in the connecting part and the wall of said rod and, at the same time, said connecting part is adapted to be fixed in position relative to said rod. As a result, it is only the action of the adjustable locking means that fixes the ligature in position and immobilizes the connecting part relative to said rod.

In one particularly advantageous embodiment of the invention, said ligature has a first end fastened to said connecting part and a free second end adapted to slide in said connecting part and to be formed into a loop, a portion of said ligature between said ends being adapted to be immobilized in translation relative to said connecting part by said adjustable locking means, whereby the loop has a particular length.

Thus the ligature is formed of two sections. One end of the ligature is fixedly clipped to the connecting part, the ligature is then stretched around the rib and/or the spinous process, and the free second end of the ligature is then inserted into said connecting part. The first section of the ligature is the part that extends from the second end into contact with the rib and/or the transverse process and the second section is the part that extends from the rib and/or the transverse process to the connecting part. As a result, the free end may be stretched to hold said connecting part against the vertebra, said rod and said ligature being adapted to be locked together by adjustable locking means.

It is preferable if said connecting part comprises two longitudinal members whose first ends are connected together so that said members may pivot relative to each other and the middle parts of their two facing faces are adapted to bear on respective opposite sides of said rod, said adjustable locking means being adapted to drive the second ends of said longitudinal members forcibly towards each other and to fix them in position relative to each other so that said two members form a clamp and grip said rod, whereby said connecting part may be fixed in position relative to said rod.

The two longitudinal members articulated to each other at their first end form a clamp such that the two middle parts of the two facing faces may be driven towards each other and grip said rod. The adjustable locking means hold the two longitudinal members pressed onto said ligature and against said rod.

It is particularly advantageous if said second ends of the two longitudinal members have, facing each other, a bore in one and a thread in the other, so that a screw may be passed through said bore and screwed into said thread and form said adjustable locking means.

Turning the screw after it has been passed through the bore and screwed into the thread therefore forcibly drives the second ends towards each other. The force immobilizing said connecting part relative to said rod and said ligature is a function of the clamping force applied by said screw.

In one particularly advantageous embodiment, said first end of said ligature is fastened to the pivot of said longitudinal members. The tension force applied to said ligature is therefore substantially equally divided between the two first ends of said longitudinal members.

It is preferable if at least one of the middle parts of said two facing faces has a first portion through which said passage passes and a second portion adapted to bear against said rod. Accordingly, said second portion of said longitudinal members of the connecting part is adapted to bear on and to be in direct contact with said rod whereas the first portion of the middle parts presses said ligature against said rod. Said connecting part is therefore perfectly fastened to said rod and fixed in position relative to it and at the same time a portion of said ligature is perfectly wedged between said rod and the wall of said passage.

It is particularly advantageous if said passage extends between two orifices in said connecting part and opening to the outside of said part so that said ligature is able to slide through said part.

Said ligature is therefore perfectly guided inside said connecting part in said passage with the result that stretching of the free second end of said ligature cannot divert said ligature from said passage, regardless of the driving angle relative to said connecting part. During the stretching of said free send end of said ligature, the adjustable locking means immobilize at least a portion of said ligature.

It is preferable if each of said middle parts of said two longitudinal members includes an orifice. Said free end of said ligature can then be inserted into one of the two orifices, stretched in the passage that extends between the two longitudinal members and said rod, and extracted via the second orifice so that it may be stretched. Pressing the two longitudinal members against said rod therefore immobilizes the ligature against the rod.

In one particularly advantageous embodiment, said passage has a section that decreases from one orifice to the other so as to be able to exert a progressive pressure on said ligature portion between said two orifices to press it against said rod.

Thus, according to this feature, the pressure of said ligature on the rod may be controlled by the adjustable locking means so that the free second end of said ligature may be forcibly stretched, to tension it. Once it has been tensioned, the adjustable locking means may be operated to immobilize the ligature completely relative to the rod and to immobilize the connecting part relative to the rod. The loop formed around the rib and/or the transverse process by said ligature is therefore of fixed size and maintains the tension in said connecting part facing the posterior wall of said vertebra.

Figure 2:
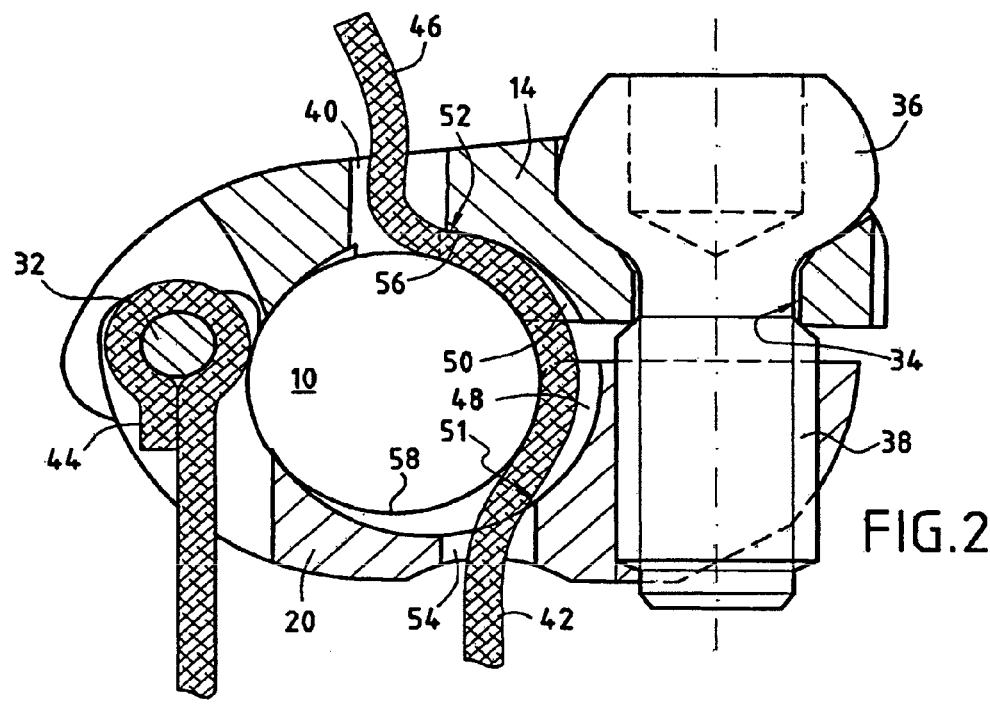
Figure 3:
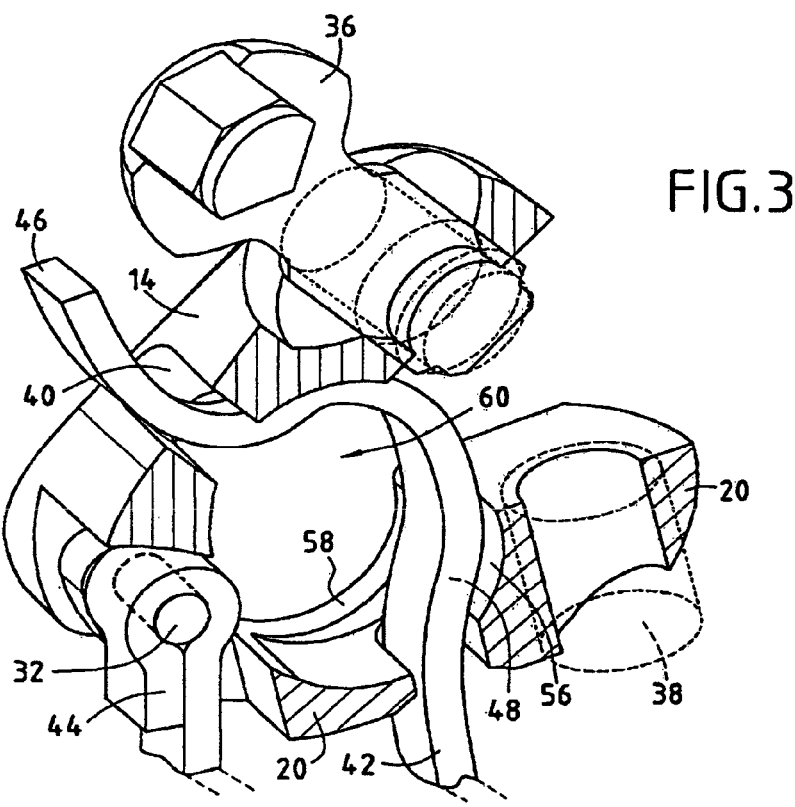
Figure 4:
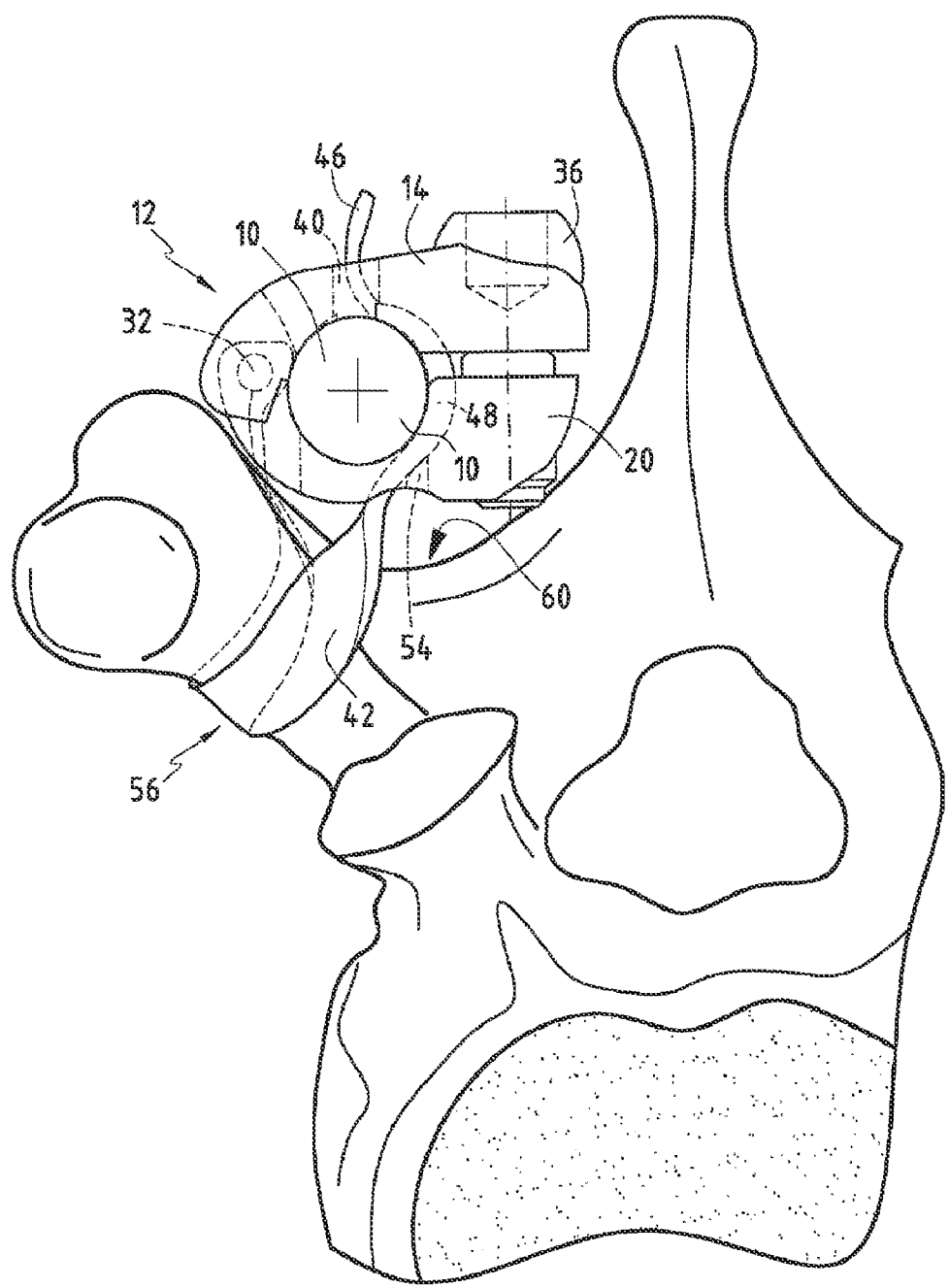

Other features and advantages of the invention will emerge upon reading the description given hereinafter and with reference to the appended drawings of particular illustrative but non-limiting embodiments of the invention, in which drawings:

FIG. 1 is a fragmentary diagrammatic perspective view showing a vertebral fixing system of the invention and a rod, FIG. 2 is a diagrammatic view in vertical section of the subject matter of the invention mounted on a rod, FIG. 3 is a diagrammatic perspective view in section of the subject matter of the invention, and FIG. 4 is a diagrammatic view in elevation of the subject matter of the invention mounted on a vertebra.

FIG. 1 shows a vertebral fixing system of the invention mounted on a rod 10. The vertebral fixing system comprises a connecting part 12 having two longitudinal members, of which a first longitudinal member 14 extends between a first end 16 and a second end 18 and a second longitudinal member 20 extends between a first end 22 and a second end 24. The two longitudinal members 14 and 20 are pivoted together at their first ends 16 and 22 for the purposes of mounting the system. The first end 16 of the longitudinal member 14 has a notch 26 with two opposite edges 28 and 30 and between which the first end 22 of the other longitudinal member 20 may be inserted. A pivot pin 32 passes through the two first ends 16 and 22 and is free to rotate in at least one of said ends 16 and/or 22. The second end 18 of the first longitudinal member 14 includes a bore 34 into which a screw 36 may be inserted. The second end 24 of the second longitudinal member 20 comprises a thread 38 which is aligned with said bore 34 when the two longitudinal members are disposed facing each other, with the result that the screw 36 may be screwed into said thread 38 in order to drive the second ends 18 and 24 of the two longitudinal members 14 and 20 towards each other. The consequences of screwing said screw 36 into the thread 38, thereby forming the adjustable locking means, are explained in more detail hereinafter. FIG. 1 also shows a first orifice 40 through which a ligature may be stretched. The method of connecting said ligature to said connecting part is described with reference to FIG. 2.

FIG. 2 shows again the connecting part 12 consisting of the first longitudinal member 14 and the second longitudinal member 20, said longitudinal members 14 and 20 pivoting about the pin 32 that joins them. The adjustable locking means consisting of said screws 36 passing through the bore 34 and screwed into the thread 38 immobilize said connecting part 12 relative to the rod 10 and fix in position a portion of a ligature 42 shown in part in FIG. 2.

The ligature 42 consists of an elongate flexible member capable of conforming to the contour of the parts that it must connect.

The ligature 42 has a first end 44 that is ligated around the pin 32 and a free second end 46 that is inserted into a passage 48 between the rod 10 and the internal walls 50 and 52 of the longitudinal members 14 and 20 and the external wall of the rod 10. As shown in FIG. 2, the second longitudinal end 20 includes a second orifice 54 through which said ligature 42 passes. Moreover, as shown in FIG. 4, the ligature 42 may be formed into a loop 56 in which the transverse process is trapped. Clearly, where applicable, the ligature 42 may also trap the rib.

As shown in FIG. 3, which shows again the second longitudinal member 20, the middle part has a first portion 56 through which said passage 48 passes and a second portion 58 adapted to bear directly on the rod. Accordingly, the passage 48, which is symmetrical inside the first longitudinal member 14, is produced by a groove formed in each of the two facing faces of the middle parts of the longitudinal members 14 and 20.

It is clear in FIG. 3 that the first portion 58 of the middle part forms an edge with cylindrical symmetry and that the corresponding second portion of the middle part of the first longitudinal member 14 forms a substantially cylindrical space 60 into which said rod 10 is inserted.

FIG. 2 shows that the second portion 58 of the middle part comes into contact with the rod and is adapted to bear on top of it and the first portion 56 presses the free second end of said ligature 42 against the rod 10. The adjustable locking means therefore drive the longitudinal members 14 and 20 forcibly against the rod 10 and simultaneously against the ligature 42, which is also forcibly pressed against the rod 10.

It is particularly advantageous if, as shown in FIG. 2, the passage 48 has a section S1 in the vicinity of the orifice 54 greater than the section S2 in the vicinity of the first orifice 40, the section of said passage 48 decreasing progressively in the direction from the second orifice 54 to the first orifice 40. The ligature 42 is therefore progressively compressed around a portion of the rod 10 with a pressure that increases in the direction from the second orifice 54 towards the first orifice 40.

FIG. 4 shows a vertebral fixing system of the invention mounted on a vertebra having a transverse process. This figure shows again the rod 10 and the two longitudinal members 14 and 20 that grip it and press a portion of the ligature 42 against said rod 10.

In FIG. 4, the flexible ligature 42 consists of a flexible strip of substantially constant width and thickness whose first end is ligated to the pin 32, the ligature surrounding the transverse process of the vertebra being inserted through the connecting part 12. The section of the flexible strip 42 is substantially rectangular so that, the pin 32 and the rod 10 being substantially perpendicular to the transverse process, the ligature has to be partly twisted in order to insert it into the passage 48 and between the ligature 32 and the point at which it contacts the transverse process. The fixing system 12 is fixed in position against the posterior wall 60 of the vertebra despite these partially twisted portions, the ligature 42 being forcibly tensioned by stretching the free second end 46.

The ligature 42 is advantageously made from a flexible material such as polyester that may be lightly crushed locally to immobilize it with a clamping effect.

A second aspect of the invention relates to a spine straightening assembly comprising a plurality of vertebral fixing systems conforming to the present invention and mounted on a plurality of successive vertebrae, on all the transverse processes of one lateral wall thereof, and connected to a single rod that is disposed substantially parallel to said spine. The transverse processes of a portion of the spine can therefore be connected together by a single longitudinal rod, to fix them in position relative to each other, by means of the above vertebral fixing system.

What is claimed is:

1. A method for compressing or distracting portions of a spine, comprising:
   positioning a connecting part on a spinal rod, wherein the spinal rod is positioned along a portion of the spine, wherein the connecting part includes a first longitudinal member and a second longitudinal member moveable relative to each other between a first position and a second position, the first longitudinal member and the second longitudinal member configured to capture the spinal rod when in the second position, and wherein at least one of the first longitudinal member and the second longitudinal member has an opening to receive at least one of a first end and a second end of a ligature therethrough;
   passing the first end of the ligature through the opening;
   passing the second end of the ligature through the opening to define a loop between the first end and the second end of the ligature, the loop extending from the connecting part to encircle a bone and being adjustable in length when the first longitudinal member and the second longitudinal member are in the first position;
   moving the first longitudinal member and the second longitudinal member relative to each other into the second position to capture the spinal rod; and
   securing the first longitudinal member and the second longitudinal member in the second position with the rod captured therebetween, the loop being fixed in length when the first longitudinal member and the second longitudinal member are secured in the second position with the rod therebetween.

2. The method according to claim 1, wherein the first longitudinal member and the second longitudinal member are connected by a hinge for movement between the first position and second position, wherein the hinge comprises a pivot pin rotatably connecting a first end of the first longitudinal member and a first end of the second longitudinal member.

3. The method according to claim 2, wherein one of the first end and the second end of the ligature is fastened to the hinge pivot pin.

4. The method according to claim 2, wherein neither of the first end or the second end of the ligature is fastened.

5. The method according to claim 1, wherein passing the at least one of the first end of the ligature and the second end of the ligature through the opening comprises passing both the first end of the ligature and the second end of the ligature through the opening and passing at least one of the first end of the ligature and the second end of the ligature into a passage proximate the spinal rod, and wherein securing the first longitudinal member and the second longitudinal member in the second position further comprises reducing the size of the passage and thereby pressing the second end of the ligature against the rod.

6. The method according to claim 1, wherein securing the first longitudinal member and the second longitudinal member in the second position further comprises rotating a screw positioned in a first bore in the first longitudinal member into a threaded bore in the second longitudinal member.

7. The method according to claim 1, wherein securing the first longitudinal member and the second longitudinal member in the second position further immobilizes the connecting part relative to the rod.

8. A method for clamping a ligature in a body, comprising the steps of:
   passing a ligature through an opening in a connecting part to form a loop extending from the connecting part, wherein the connecting part further comprises two longitudinal members moveable relative to each other, and wherein the two longitudinal members form a substantially cylindrical space into which a spinal rod is inserted;
   tensioning the ligature so a portion thereof is pressed against the spinal rod inserted in the substantially cylindrical space in the connecting part; and
   driving the two longitudinal members together to hold the ligature and the spinal rod in place relative to the connecting part, wherein the two longitudinal members are connected via a pin at a first end and an adjustable locking means at a second end of the connecting part.

9. The method according to claim 8, wherein the two longitudinal members are movable relative to each other between a first position and a second position, wherein the two longitudinal members comprise a first longitudinal member and a second longitudinal member, and wherein the adjustable locking means comprises:

a first bore through a second end of the first longitudinal member;

a threaded bore through a second end of the second longitudinal member that is aligned with the first bore when the first and second longitudinal members are in the second position; and a screw positioned in the first bore configured to be received in the threaded bore upon rotation, wherein driving the first longitudinal member and the second longitudinal member together comprises turning the screw in the thread.

10. The method according to claim 8, wherein the two longitudinal members are movable relative to each other about the pin.

11. The method according to claim 8, wherein an end of the ligature is fastened to the pin.

12. The method according to claim 8, wherein neither ends of the ligature is fastened.

13. A method for placing a vertebral fixing system on a vertebra, comprising:

passing a ligature through a connecting part of the vertebral fixing system to form a loop extending from a first side of the connecting part, wherein at least one end of the ligature extends from a second side of the connecting part, wherein the loop surrounds a transverse process of the vertebra, and wherein the connecting part further comprises two members moveable relative to each other;

tensioning the ligature by stretching the at least one end of the ligature extending from the second side of the connecting part to fix the connecting part in position against a posterior wall of the vertebra; and driving the two longitudinal members together to hold the ligature in place relative to the connecting part, wherein the two longitudinal members are connected via a pin at a first end and an adjustable locking means at a second end of the connecting part.

14. The method according to claim 13, wherein the two longitudinal members form a substantially cylindrical space into which a spinal rod is inserted and wherein when the ligature is tensioned a portion thereof is pressed against the spinal rod inserted in the substantially cylindrical space in the connecting part.

15. The method according to claim 14, wherein the two longitudinal members are driven together against the spinal rod and simultaneously against the ligature.

16. The method according to claim 14, wherein the ligature is progressively compressed around a portion of the spinal rod with a pressure that increases in the direction from the first side of the connecting part towards the second side of the connecting part.

17. The method according to claim 14, further comprising:

fastening the adjustable locking means to immobilize the connecting part relative to the spinal rod and fix in position a portion of the ligature.

18. The method according to claim 13, wherein the two longitudinal members are movable relative to each other about the pin prior to being driven together to hold the ligature in place relative to the connecting part.

19. The method according to claim 13, further comprising crushing a portion of the ligature to immobilize it with a clamping effect.

20. The method according to claim 13, wherein the vertebral fixing system is one of a plurality of vertebral fixing systems mounted on a plurality of successive vertebrae, on all transverse processes of one lateral wall thereof, and connected via a single spinal rod, and wherein the spinal rod is disposed substantially parallel to the spine.

21. A method for securing a bone to a rod, comprising:
a) placing a connecting part on a rod;
b) passing a first end of a ligature around a bone;
c) passing the first end of the ligature through the connecting part to form a loop extending from a first side of the connecting part, the first end extending from a second side of the connecting part;
d) tensioning the ligature to fix the connecting part in position relative to the bone;
e) securing the ligature to the connecting part by pressing the ligature against an interior surface of the connecting part; and
f) tightening a threaded fastener in the connecting part to fix the rod in position relative to the connecting part, thereby securing the bone to the rod, wherein the threaded fastener does not contact the ligature when the connecting part is fixed to the rod.

22. The method according to claim 21, further comprising:
repeating steps a)-f) to secure at least a second bone to the rod via at least a second ligature and a second connecting part.

23. The method according to claim 21, further comprising:
repeating steps a)-f) multiple times to secure a plurality of successive vertebrae, on all transverse processes of one lateral wall thereof, to the rod, wherein each of the plurality of successive vertebrae is secured to the rod via a corresponding ligature and a corresponding connecting part.

24. The method according to claim 23, wherein the rod is disposed substantially parallel to a spine, thereby connecting the transverse processes of a portion of the spine together by the rod to fix them in position relative to each other.

* * * * *